US008095222B2

(12) United States Patent
Baker et al.

(10) Patent No.: US 8,095,222 B2
(45) Date of Patent: *Jan. 10, 2012

(54) MEDICAL INSTRUMENTS AND TECHNIQUES FOR TREATMENT OF GASTRO-ESOPHAGEAL REFLUX DISEASE

(76) Inventors: James A. Baker, Palo Alto, CA (US); John H. Shadduck, Tiburon, CA (US)

( * ) Notice: Subject to any disclaimer, the term of this patent is extended or adjusted under 35 U.S.C. 154(b) by 1201 days.

This patent is subject to a terminal disclaimer.

(21) Appl. No.: 11/656,062

(22) Filed: Jan. 22, 2007

(65) Prior Publication Data
US 2007/0118109 A1 May 24, 2007

Related U.S. Application Data

(60) Division of application No. 10/375,505, filed on Feb. 27, 2003, now Pat. No. 7,167,758, which is a division of application No. 09/648,345, filed on Aug. 25, 2000, now Pat. No. 6,535,768, which is a continuation of application No. 09/258,006, filed on Feb. 25, 1999, now Pat. No. 6,197,022, which is a continuation of application No. 08/920,291, filed on Aug. 28, 1997, now Pat. No. 5,957,920.

(51) Int. Cl.
*A61F 2/00* (2006.01)
(52) U.S. Cl. ........................................ 607/101; 607/102
(58) Field of Classification Search ............... 606/31, 606/33, 41–52; 607/96, 101–102
See application file for complete search history.

(56) References Cited

U.S. PATENT DOCUMENTS

| | | | |
|---|---|---|---|
| 4,396,019 A | 8/1983 | Perry, Jr. | |
| 5,103,804 A | 4/1992 | Abele et al. | |
| 5,151,100 A * | 9/1992 | Abele et al. | 606/28 |
| 5,191,883 A * | 3/1993 | Lennox et al. | 607/102 |
| 5,249,585 A | 10/1993 | Turner et al. | |
| 5,341,807 A | 8/1994 | Nardella | |
| 5,395,363 A | 3/1995 | Billings et al. | |
| 5,397,321 A | 3/1995 | Houser et al. | |
| 5,425,364 A | 6/1995 | Imran | |
| 5,443,470 A | 8/1995 | Stern et al. | |
| 5,454,782 A | 10/1995 | Perkins | |
| 5,496,271 A * | 3/1996 | Burton et al. | 607/27 |
| 5,540,655 A | 7/1996 | Edwards | |
| 5,571,153 A * | 11/1996 | Wallsten | 607/98 |
| 5,575,787 A | 11/1996 | Abela et al. | |
| 5,575,788 A | 11/1996 | Baker et al. | |
| 5,620,480 A * | 4/1997 | Rudie | 607/101 |
| 5,651,785 A | 7/1997 | Abela et al. | |
| 5,657,755 A | 8/1997 | Desai | |
| 5,658,278 A | 8/1997 | Imran et al. | |
| 5,681,280 A | 10/1997 | Rusk et al. | |
| 5,688,267 A | 11/1997 | Panescu et al. | |
| 5,716,340 A | 2/1998 | Schweich, Jr. et al. | |
| 5,718,666 A | 2/1998 | Alarcon | |

(Continued)

*Primary Examiner* — Roy Gibson
(74) *Attorney, Agent, or Firm* — Ryan Kromholz & Manion, S.C.

(57) ABSTRACT

Apparatus and methods for treating tissue at or near a sphincter provide for transluminal introduction of an energy delivery device. The device includes a tissue compression member to compress target tissue at or near the sphincter. A radiofrequency energy source is coupleable to the delivery device to deliver radiofrequency energy to the target tissue. Energy is delivered to heat the tissue to a desired temperature. The desired temperature is selected to induce an injury-healing response or to inducing shrinkage of collagen fibers in the target tissue to thereby reduce laxity in the target tissue.

1 Claim, 11 Drawing Sheets

U.S. PATENT DOCUMENTS

| | | |
|---|---|---|
| 5,785,705 A | 7/1998 | Baker |
| 5,800,429 A | 9/1998 | Edwards |
| 5,830,179 A | 11/1998 | Mikus et al. |
| 5,891,027 A | 4/1999 | Tu et al. |
| 5,891,134 A | 4/1999 | Goble et al. |
| 5,897,553 A | 4/1999 | Mulier |
| 5,947,964 A | 9/1999 | Eggers et al. |
| 5,957,920 A | 9/1999 | Baker |
| 6,006,755 A | 12/1999 | Edwards |
| 6,009,877 A | 1/2000 | Edwards |
| 6,015,407 A | 1/2000 | Rieb et al. |
| 6,033,397 A | 3/2000 | Laufer et al. |
| 6,044,846 A | 4/2000 | Edwards |
| 6,056,744 A | 5/2000 | Edwards |
| 6,066,139 A | 5/2000 | Ryan et al. |
| 6,073,052 A * | 6/2000 | Zelickson et al. ............ 607/100 |
| 6,091,995 A | 7/2000 | Ingle et al. |
| 6,092,528 A | 7/2000 | Edwards |
| 6,254,598 B1 | 7/2001 | Edwards et al. |
| 6,363,937 B1 | 4/2002 | Hovda et al. |
| 6,401,719 B1 | 6/2002 | Farley et al. |
| 6,405,732 B1 | 6/2002 | Edwards et al. |
| 6,411,852 B1 | 6/2002 | Danek et al. |

\* cited by examiner

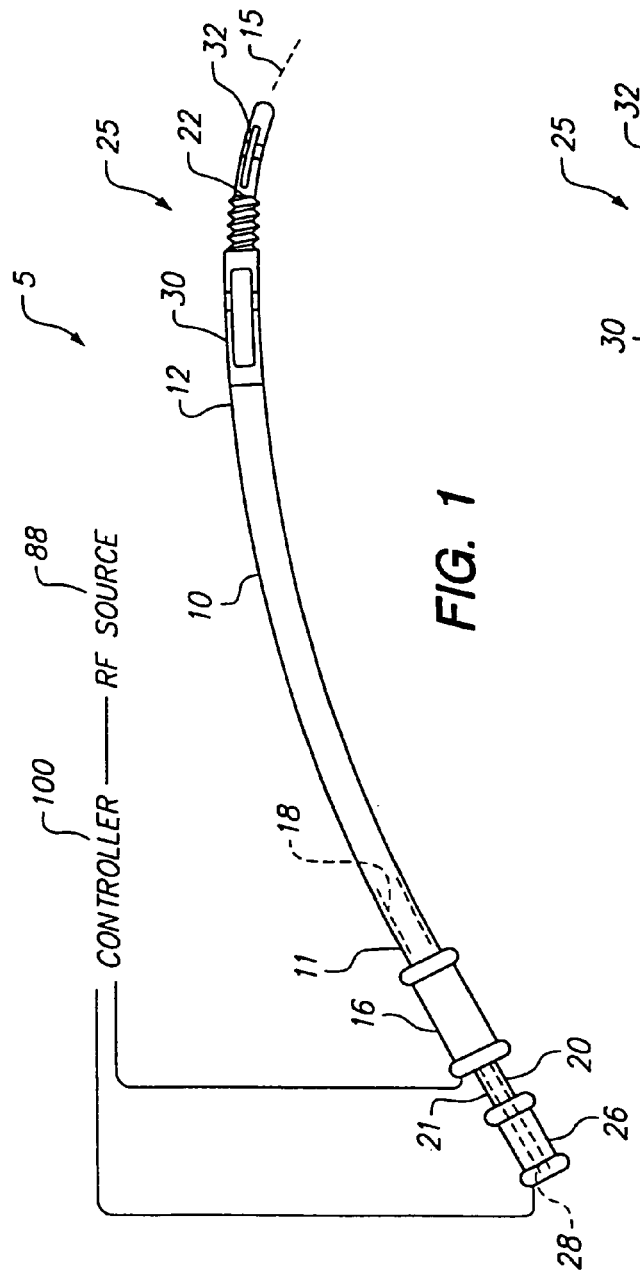
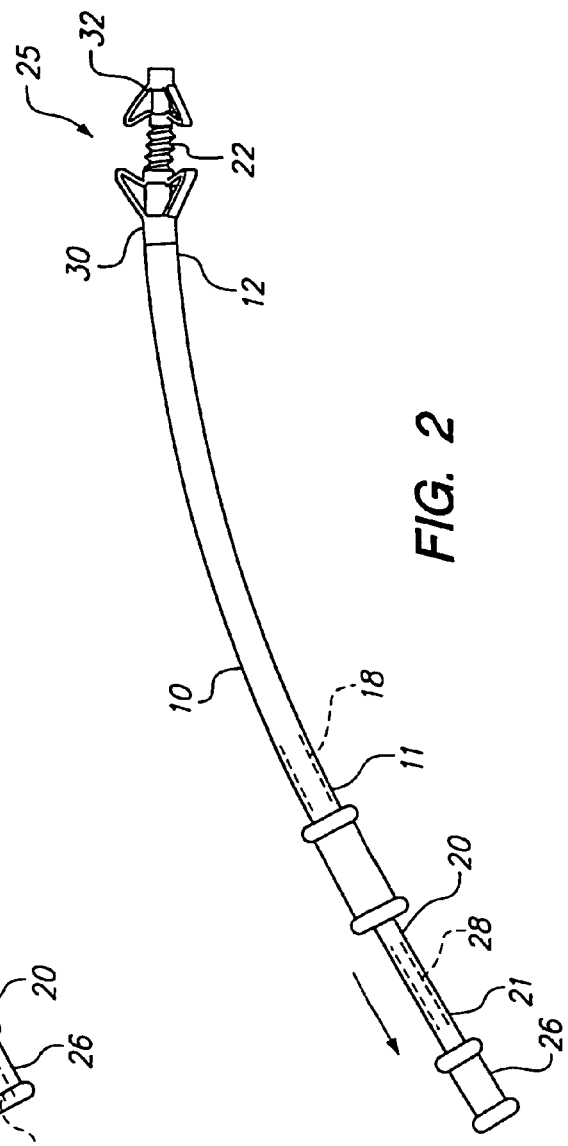

MEDICAL INSTRUMENTS AND TECHNIQUES FOR TREATMENT OF GASTRO-ESOPHAGEAL REFLUX DISEASE

CROSS-REFERENCE TO RELATED APPLICATIONS

This application is a divisional of application Ser. No. 10/375,505, filed Feb. 27, 2003 (now U.S. Pat. No. 7,167,758), which is a divisional of application Ser. No. 09/648,345, filed Aug. 25, 2000 (now U.S. Pat. No. 6,535,768), which is a continuation of application Ser. No. 09/258,006 filed Feb. 25, 1999 (now U.S. Pat. No. 6,197,022), which is a continuation of application Ser. No. 08/920,291, filed Aug. 28, 1997 (now U.S. Pat. No. 5,957,920). This application relates to the invention disclosed in provisional Application Ser. No. 60/024,974 filed Aug. 30, 1996 and is also related to provisional Application Ser. No. 60/022,790 filed Jul. 30, 1996, both of which by this reference are incorporated herein.

FIELD OF THE INVENTION

This invention relates to unique therapeutic instruments and techniques for delivering thermal energy to a target tissue volume or site in an interior of a patient's body in a "non-invasive" manner for medical purposes, such as selective cell damage, cell necrosis, molecular contraction or tissue stimulation. An exemplary embodiment of the invention is a catheterlike device with a working portion that can be introduced in a patient's urethra in a treatment for urinary incontinence. A treatment for gastroesophageal reflux disease also may be fashioned to increase the rigidity or the length of the lower esophageal sphincter (LES) by laying down a fiber matrix around the LES. The device delivers thermal energy to "subsurface" or extraluminal tissues at a precise pre-selected "target" site, at the same time minimizing trauma to the wall around the lumen as well as tissues outward from the "target" site. The principal use of the exemplary embodiment is to selectively damage cells around a patient's sphincter which thereafter causes population of the extracellular compartment of the injury site with a collage fiber matrix. The collagen matrix serves as a means of altering cellular architecture and thus the bio-mechanical characteristics of the sphincter. The instrument of the invention also may be used to hydrothermally shrink such collagen fiber matrices in a periodic treatment cycle to further "model" target tissue flexibility to further alter the bio-mechanics of the sphincter.

SUMMARY OF THE INVENTION

According to one aspect of the invention, an apparatus to treat a target tissue volume at or near a sphincter comprises a radiofrequency energy delivery device. The delivery device has a working end sized and configured for transluminal introduction into a patient and includes a tissue compression member deployable to provide compression of target tissue at or near a sphincter. A radiofrequency energy source is coupleable to the delivery device to deliver radiofrequency energy to the target tissue to reduce laxity in the target tissue. In one embodiment, the delivery device does not penetrate a wall of a body lumen.

The tissue compression member may take various forms, such as a laterally extending extendable element or an inflatable structure. Compression of the target tissue modifies the extracellular fluid content of the target tissue to alter the tissue's resistance to electrical energy. Compression of target tissue decreases the level of extracellular fluid content of the tissue to increase the target tissue's resistance to radiofrequency energy while contemporaneously increasing the extracellular fluid level in the surrounding tissue volume.

Energy is delivered to heat the targeted tissue to a desired temperature. The desired temperature may be selected to stimulate an injury-healing response that populates the targeted tissue with collagen fiber matrix in extracellular space.

Alternatively, the desired temperature may be selected to induce shrinkage of collagen fibers in the target tissue, e.g., in response to denaturing, cleaving or partially denaturing intermolecular cross-link or hydrogen bonds.

Another aspect of the invention provides a method of treating tissue at or near a sphincter. A thermal energy delivery device having a tissue compression member is introduced through a body lumen to a targeted tissue site at or near a sphincter. The tissue compression member is deployed to provide compression of the target tissue at or near a sphincter. Radiofrequency energy is delivered to the targeted tissue to induce an injury-healing response. In one embodiment, energy is also be delivered to induce shrinkage of collagen fibers in the targeted tissue.

Other subjects and objects of this disclosure relate to novel techniques and instruments for the controlled modeling or remodeling of cellular architectures in the interior of a patient's body to alter the structural support of tissue layers, the support within anatomic structures such as organs or body conduits, or to alter the biomechanical characteristics of tissue masses or volumes in the interior of the body, including but not limited to soft tissues, organs and lumened structures (e.g., esophagus, urethra), such tissues hereafter referred to as a "target" tissue volume or mass.

In the prior art, site-specific thermal treatment of cellular tissues in the interior of a patient's body generally require direct contact of the targeted cellular tissues with a medical device such as an thermal electrode, usually by a surgical procedure that exposes both the targeted cellular tissue and intervening tissue to trauma. For example, various microwave, radiofrequency and light energy (laser) devices have been developed for intraluminal use to thermally treat intraluminal tissues as well as extraluminal tissue volumes to destroy malignant, benign and other types of cells and tissues in a wide variety of anatomic sites. Tissues treated include isolated carcinoma masses, and more specifically, organs such as the prostate. Such prior art devices typically include a catheter or cannula which is used to carry a radiofrequency electrode or microwave antenna through an anatomic duct or conduit to the region of treatment to apply energy directly through the conduit wall into the surrounding tissue in all directions. Severe trauma often is sustained by the duct wall during the thermal energy delivery to extraluminal target tissues. Some prior art devices combine cooling systems to reduce trauma to the conduit wall. Such cooling mechanisms complicate the device and require that the device be sufficiently large to accommodate this cooling system. Other prior art devices use catheters with penetrating elements that are extendable through the duct wall to access the target tissue mass, such as a device for treating benign prostatic hyperplasia.

More in particular, the present invention discloses "non-invasive" techniques and instruments that utilize thermal energy to selectively damage or injure certain cells in a site-specific volume in the interior of a body. By the term non-invasive, it is meant that the working end of the device does not penetrate the interior of the body through any incision in tissue. The non-invasive working end of the device still may be disposed in the interior of the body by passing through an orifice into a lumen or duct in a body-however, the device will not penetrate a wall of the orifice.

The non-invasive selective damage to cells in target tissues induces a biological response to the injury. Such a biological response includes cell reproduction or repopulation along with the proliferation of a fiber matrix of collagen in the extracellular space. Thus, the controlled modeling of the structural or mechanical characteristics of targeted tissue volume is possible by creation of such a collagen fiber matrix therein. Such selective injury to particular cell volume is accomplished by modifying the extracellular fluid content (ECF) so as to increase its resistance (R) to RF energy when compared to the surrounding tissue volume, thus causing site-specific thermal energy delivery to selectively injure a certain cell population.

Various terms may be suitable for describing either elements of the process of thermal modeling of tissue by altering the bio-mechanical characteristics of the targeted tissue volume with the creation of a collagen matrix in the extracellular space. Terms such as inducing connective tissue formation, aggregating fibrous tissue, inducing the formation of scar tissue, tissue massing or tissue bulking, fibrosis, fibrogenesis, fibrillogenesis, etc. have been used.

Various other terms have been used to describe the thermal effects on collagen molecules or fibers in the interior of the body and deal with dimensional changes—such as tissue shrinkage, molecular (both intra- and intermolecular) shrinkage, cellular (both intra- and extracellular) shrinkage or contraction, contracture, etc. For clarity of presentation, this disclosure will use the terms "modeling" to describe an object of a treatment. Other various terms relating to the formation of a extracellular "collage matrix" or "matrices" having "fiber" characteristics will be used for the purpose of describing more specific objects of the invention. When referring to reducing dimensional changes in a tissue volume, whether at the cellular or intracellular level, the terms "shrinkage" or "contraction" will be used. These terms are thus inclusive of the aforementioned words, and all other phrases and similar terms that relate to biophysical phenomena of collagen matrix formation and tissue modeling described in more detail below. The above described objects or the invention are accomplished by controlled manipulation of bio-physical actions or phenomena relating to (i) induction of the injury healing response within a tissue volume in the interior of a body to populate the volume with a collagen fiber matrix of in the extracellular space. The objects of the invention further include (ii) the selective hydrothermal shrinkage of collagen fibers in the target tissue volume of surrounding tissue volumes subsequent to, or during, the injury healing response.

As background, the injury healing response in a human body is complex and first involves an inflammatory response. A very mild injury will produce only the inflammatory reaction. More extensive tissue trauma—no matter whether mechanical, chemical or thermal—will induce the injury healing response and cause the release of intracellular compounds into the extracellular compartment at the injury site. This disclosure relates principally to induction of the injury healing process by thermal energy delivery; the temperature required to induce the process ranging from about 45° to 65° C. depending on the target tissue and the duration of exposure. Such a temperature herein is referred to as $T_{cd}$ (temperature level that causes "cell damage" to induce the injury healing response). It is important to note that the temperature necessary to cause cell damage may be substantially lower than the temperature ($T_{sc}$) necessary to shrink collagen fibers described below.

In order to selectively damage cells to induce the population of the extracellular compartment with a collagen fiber matrix, "control" of the injury to a particular tissue volume mass is essential. In this disclosure, a thermal energy source is provided to selectively induce the injury healing response, and more particularly an RF source. (It should be appreciated that other thermal energy devices are possible, for example a laser with or without a diffuser mechanism, or shortwave, microwave or ultrasound). In an RF energy delivery mechanism, a high frequency alternating current (e.g., from 100,000 Hz to 500,000 Hz) is adapted to flow from a series of parallel electrodes into tissue. The alternating current causes ionic agitation and friction in the target tissue mass as the ions follow the changes in direction of the alternating current. Such ionic agitation or frictional heating thus does not result from direct tissue contact with an electrode. In the delivery of energy to a soft tissue mass, I=E/R where I is the intensity of the current in amperes, E is the energy potential measured in volts and R is the tissue resistance measured in ohms. In such a soft tissue mass, "current density" or level of current intensity is an important gauge of energy delivery which relates to the impedance of the tissue mass ($I_{tc}$ is impedance of target cells). The level of heat generated within the target tissue mass thus is influenced by several factors, such as (i) RF current intensity, (ii) RF current frequency, (iii) cellular impedance ($I_{tc}$) levels within the target cells, (v) heat dissipation from the target tissue mass; duration of RF delivery, and (vi) distance of the tissue mass from the electrodes. Thus, an object of the present invention is the delivery of "controlled" thermal energy to a target tissue volume by utilizing a computer-controlled system to vary the duration of current intensity and frequency based on sensor feedback mechanisms.

The novel techniques disclosed herein also delivery thermal energy in (i) a site-specific manner to a target tissue volume, and (ii) in a manner that does not injure surface tissue while at the same time delivering sufficient energy to damage subsurface cells. The novel techniques are adapted to manipulate (compress or decompress) the target tissue volume to alter regional cell or tissue impedance ($I_{tc}$). More particularly, in soft tissues which are the subject of this disclosure, there is a varying amount of extracellular fluid (ECF) that has a measurable ECF level. By altering the ECF level, and/or the ionic character of the fluid, the thermal energy that is delivered to a target site will generate differing levels of extracellular temperature resulting in altered levels of cell damage (from different current density). For example, mechanical compression of a target tissue volume will lower the volume's ECF level in a subsurface site-specific region, the tissue volume thus increasing in impedance ($I_{tc}$) and becoming more of a resistor. At the same time, the surface tissues are less susceptible to ECF alteration by such mechanical compression which allows the temperature in the subsurface target volume to reach the $T_{cd}$ (cell damage temperature) without ablation of the surface layer.

In the initial cellular phase of injury healing, granulocytes and macrophages appear and remove dead cells and debris. In the subsequent early stages of inflammation, the inflammatory exudate contains fibrinogen which together with enzymes released from blood and tissue cells, cause fibrin to be formed and laid down in the area of the injury. The fibrin serves as a hemostatic barrier and acts as a scaffold for repair of the injury site. Thereafter, fibroblasts migrate and either utilize the fibrin as scaffolding or for contact guidance thus further developing a fiber-like scaffold in the injury area. The fibroblasts not only migrate to the injury site but also proliferate. During this fibroplastic phase of cellular level repair, an extracellular repair matrix is laid down that is largely comprised of collagen. Depending on the extent of the injury to tissue, it is the fibroblasts that synthesize collagen within the extracellular compartment as a connective tissue matrix including collage (hereafter nascent collagen), typically commencing about 36 to 72 hours after the injury.

Thus, in the healing response in a human body, tissue repair occurs principally by fibrous tissue proliferation rather organ regeneration. Most compound tissues or organs (e.g., epithelium which is a tissue) are repaired by such fibrous connective tissue formation. Such connective tissue matrices are the single most prevalent tissue in the body and give structural rigidity or support to tissue masses or layers. The principal components of such connective tissues are three fiber-like proteins-principally collagen, along with reticulin, elastin and a ground substrate. The bio-mechanical properties of fibrous connective tissue and the repair matrix are related primarily to the fibrous proteins of collagen and elastin. As much as 25% of total body protein is native collagen. In repair matrix tissue, it is believed that nascent collagen is well in excess of 50%.

A brief description of the unique properties of collagen is required. Collagen (native) is an extracellular protein found in connective tissues throughout the body and thus contributes to the strength of the musculo-skeletal system as well as the structural support of organs. Five types of collagen have been identified that seem to be specific to certain tissues, each differing in the sequencing of amino acids in the collagen molecule. Type I collagen is most commonly found in skin, tendons, bones and other connective tissues of the integument. Type III collagen is most common in muscles and other more elastic tissues.

It has been previously recognized that collagen (or collagen fibers as later defined herein) will shrink or contract when elevated in temperature to the range about 22 to 30 degrees above normal body temperature, herein referred to as $T_{sc}$ (temperature to shrink collagen) (about 60° to 70° C.).

Extracellular collagen consists of a continuous helical molecule made up of three polypeptide coil chains. Each of the three chains is approximate equal length with the molecule being about 1.4 nanometers in diameter and 300 nm, in length along its longitudinal axis in its helical domain (medial portion of the molecule). The spatial arrangement of the three peptide chains is unique to collagen with each chain existing as a right-handed helical coil. The superstructure of the molecule is represented by the three chains being twisted into a left-handed superhelix. The helical structure of each collagen molecule is bonded together by heat labile intermolecular cross-links (or hydrogen cross-links) between the three peptide chains providing the molecule with unique physical properties, including high tensile strength along with moderate elasticity. Additionally, there exists at one heat stabile or covalent cross-link between the individual coils. The heat labile cross-links may be broken by mild thermal effects thus causing the helical structure of the molecule to be destroyed (or denatured) with the peptide chains separating into individual randomly coiled structures. Such thermal destruction of the cross-links results in the shrinkage of the collagen molecule along its longitudinal axis to approximately one-third of its original dimension. The contraction of collagen fibers at from 60° C. to 70° C. is alternatively referred to as denaturing, cleaving or partially denaturing the intermolecular cross-links or hydrogen bonds.

A plurality of collagen molecules (also called fibrils) aggregate naturally to form collagen fibers that collectively make up the fibrous repair matrix. The collagen fibrils polymerize into chains in a head-to-tail arrangement generally with each adjacent chain overlapping another by one-forth the length of the helical domain in a quarter stagger fashion. The chains overlap in three dimensions and each collagen fiber reaches a natural maximum diameter, it is believed because the entire fiber is twisted resulting in an increased surface area such that succeeding layers of collagen molecules cannot bond with contact points on underlying layers in the quarter-stagger arrangement.

It is believed that there exist pre-denaturational changes in collagen fibrils and fibers due to elevation of heat which include (i) initial destabilization of the intramolecular cross-links, (ii) destabilization of the intermolecular cross-links, (iii) partial helix-to-coil transformations associated with denaturation of some or both intramolecular and intermolecular cross-links, and (iii) complete denaturation of some, but not all, molecules making up a collagen fibrils. Such pre-denaturational changes all result in partial contraction or shrinkage of collagen fibers in a collagen-containing tissue volume. By the term "partial denaturation" or "at least partial denaturation" as used herein which are associated with a method of the invention, it is meant that at least some (but probably not all) of the heat labile crosslinks of the collagen molecules making up a collagen fiber are destabilized or denatured thus causing substantial contraction of collagen fibers in a tissue mass. It is believed that such at least partial denaturation of the collagen fibers will result in shrinkage of the collagen and "tightening" of a collagen-containing tissue volume up to about 50 to 60 percent of its original dimensions (or volume).

Thus, the present invention is directed to non-invasive techniques and instruments for controlled thermal energy delivery to a selected tissue volume in the interior of a body to: (i) selectively injure certain cells in the target tissue volume to induce the biological injury healing response to populate the extracellular compartment with a fiber matrix thereby altering the structural support or flexibility characteristics of the target tissue volume; and optionally (ii) to cause the shrinkage of either "native" collagen or "nascent" collagen in the tissue volume to further alter bio-mechanical characteristics of the tissue volume.

More in particular, the thermal energy delivery (TED) device of the present invention has a catheter-like form with a proximal control end and a distal working portion dimensioned for transluminal introduction. The working portion has radiused laterally-extending elements that are deployable to engage target issues on either side of the patient's sphincter. RF electrodes are carried on the working faces of the opposing laterally-extending elements for delivering thermal energy to the target tissues. Thus, the working portion of device is capable of sitespecific compression of the target tissue to decrease the level of extracellular fluid (ECF) of the tissue to increase its resistance to RF energy. What is important is that the resistance is increased only locally within the target tissue volume by lowering of the ECF level while contemporaneously increasing the ECF level in the surrounding tissue volume. Thus, the interior of the target tissue may be thermally elevated to a $T_{cd}$ (temperature for cell damage) while at the same time the wall surface around the urethra should not be ablated due by the thermal energy delivery.

The therapeutic phase commences and is accomplished under various monitoring mechanisms, including but not limited to (i) direct visualization, (ii) measurement of tissue impedance of the target tissue volume, and (iii) utilization of ultrasound imaging before and during treatment. The physician actuates the pre-programmed therapeutic cycle for a period of time necessary to elevate the target tissue volume to $T_{cd}$ (temperature of cellular damage) which is from 45° to 65° depending on duration.

During the therapeutic cycle, the delivery of thermal energy is conducted under full-process feedback control. The delivery of thermal energy induces the injury healing response which populates the volume with an extracellular collagen matrix which after a period of from 3 days to two weeks increases pressure on the sphincter. The physician may thereafter repeat the treatment to further model the cellular architecture around the sphincter.

In subsequent therapeutic treatment cycles, the delivery of thermal energy may be elevated to at least partially denature collagen fibers in the extracellular matrix without damage or substantial modification of surrounding tissue masses at a range between 60° to 80° C. The effect of collagen shrinkage will further stiffen the treated tissue volume to further increase extraluminal pressures on the sphincter.

In general, the present invention advantageously provides technique and devices for creating preferential injury to a cellular volume in a subsurface target tissue.

The present invention provides techniques and instruments for altering the flexibility or bio-mechanical characteristics of subsurface target tissues.

The present invention provides a novel non-invasive devices and techniques for thermally inducing the injury healing process in the interior of the body without penetration of a tissue wall with an instrument.

The present invention provides an instrument and technique for modifying extracellular fluid content (ECF) of a target tissue volume to alter the tissue's resistance to electrical energy.

The present invention advantageously provides an electrode array for elevating current density from an electromagnetic (thermal) energy source in "surface" tissues to a lesser level while simultaneously elevating current density in "subsurface" tissues to a higher level.

The present invention advantageously provides a thermal energy delivery device which gives the operator information about the temperature and other conditions created in both the tissue targeted for treatment and the surrounding tissue.

The present invention provides a device that is both inexpensive and disposable.

BRIEF DESCRIPTION OF THE DRAWINGS

FIG. 1 is an elevational view of a the present invention with the working portion in an insertion configuration.

FIG. 2 is an elevational view of device of FIG. I with the working portion in a deployed configuration.

FIG. 7A being a sectional views of the initial step of introducing the device into the urethra; FIG. 7B being a view of actuating certain laterally-extending elements of the working portion in the patient's bladder; FIG. 7C being a view of actuating certain laterally-extending elements of the working portion in the patient's urethra; FIG. 7D being a view of approximating the laterally-extending elements to compress tissue therebetween to alter extracellular fluid content therein to facilitate an electrosurgical treatment.

DETAILED DESCRIPTION OF THE INVENTION

Figure 3:
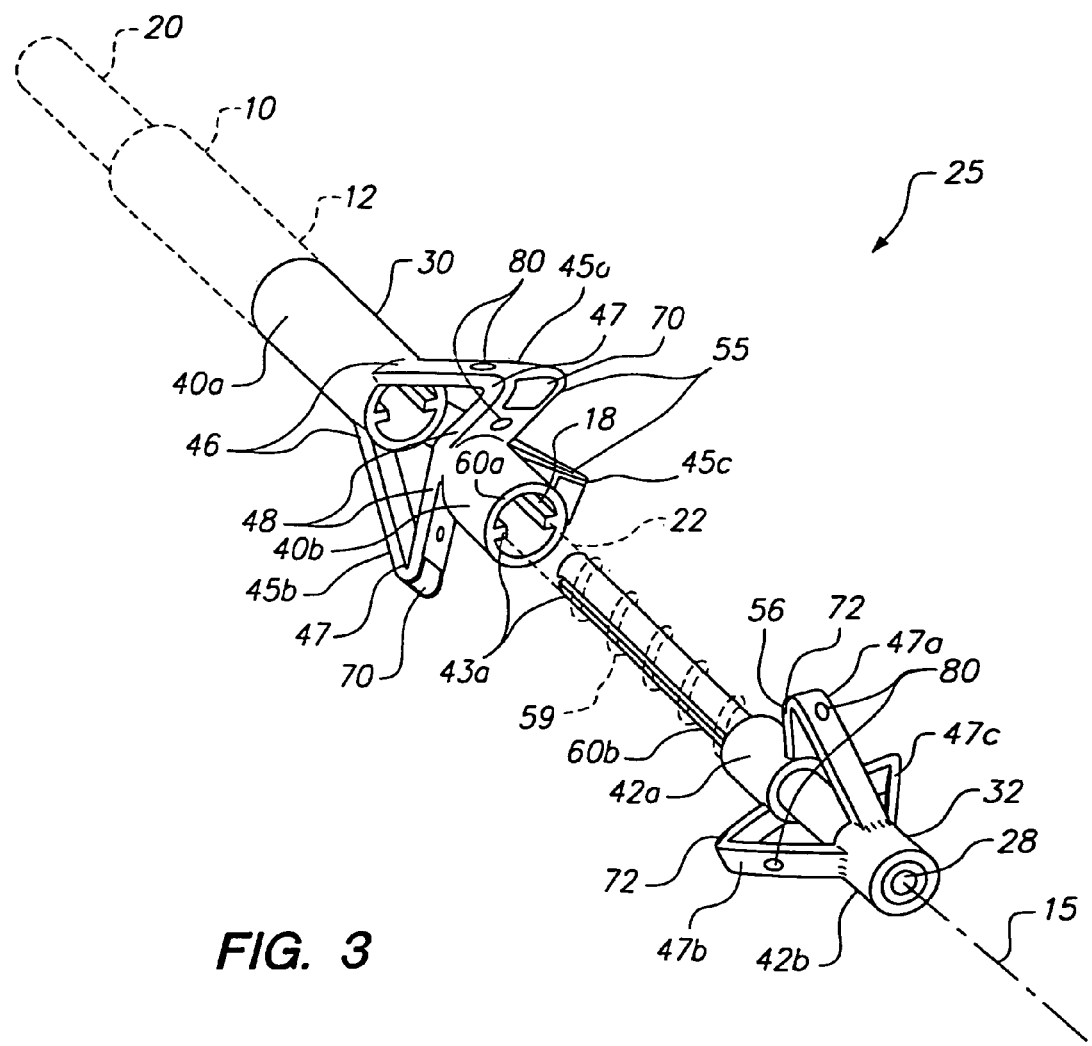
FIG. 3 is an enlarged perspective view of components of the working portion of the device of FIG. 1 de-mated from one another.

I. Type "A" Embodiment of Thermal Energy Delivery (TED) Device

Referring to FIG. 1, a Type "A" embodiment of the present invention is shown that is adapted for transluminal introduction to treat specific target tissue regions around a patient's sphincter. As shown in FIG. 1, thermal energy delivery (TED) system 5 comprises elongate flexible outer catheter sleeve 10 dimensioned for transluminal passage with proximal end 11 and distal and 12 and extending along axis 15. First distal handle portion 16 is coupled to proximal end 11 of the outer sleeve. Catheter 10 has axial lumen 18 extending therethrough for accommodating the reciprocation of co-axial inner sleeve 20 with working portion 25 coupled to both inner and outer sleeves as described below. Second proximal handle portion 26 is coupled to proximal end 21 of the inner sleeve 20. Inner sleeve 20 with proximal end 21 and distal end 22 has (optional) lumen 28 therein dimensioned to slidably receive a fiberscope or so that system 5 may be introduced over a guide catheter or scope (not shown).

Figure 4A:
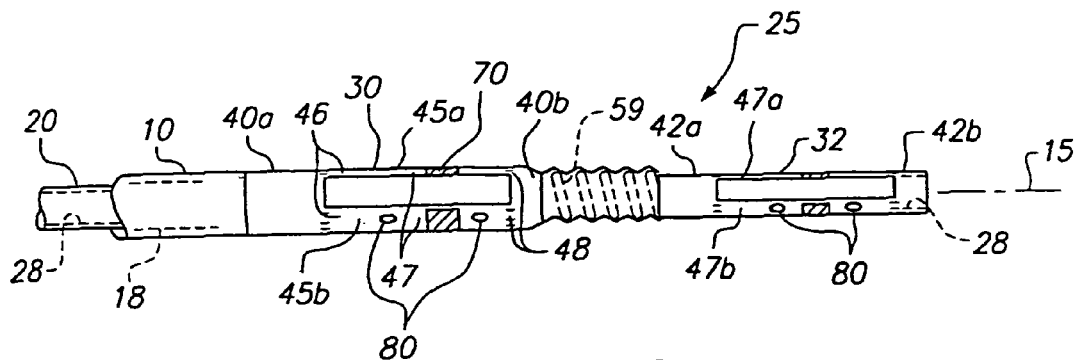
FIGS. 4A-4C are enlarged elevational views of the components of the working portion of FIG. 1 in various positions.

Referring to FIGS. 3 and 4A, working portion 25 of system 5 comprises two cooperating tissue-engaging or tissue-compression members 30 and 32 of any suitable material and is described in this embodiment as made of a flexible plastic material. FIG. 3 shows tissue-compression members 30 and 32 de-mated from one another and de-mated from outer and inner catheter sleeves, 10 and 20. Proximal member 30 is coupled to distal end 12 of outer sleeve 10. Distal tissue-compression member 32 is coupled to distal end 22 of inner sleeve 10. Tissue-compression member 30 has proximal end 40*a* and distal end 40*b* and tissue-compression member 32 has proximal end 42*a* and distal end 42*b*. FIG. 3 also shows a plurality of cooperating longitudinal keys 43*a* (collectively) in members 30 and 32 maintain angular registration between the tissue compression members and allows for their axial reciprocation relative to one another as described below.

Figure 4B:
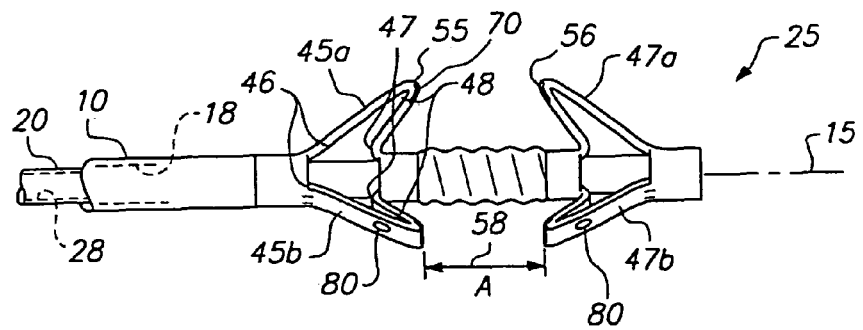
Figure 4C:
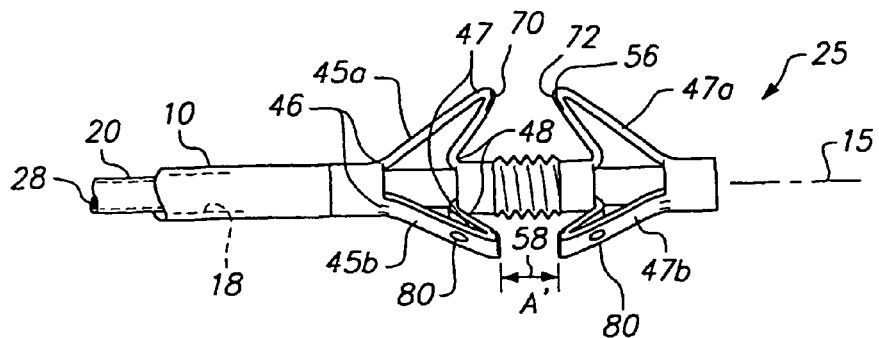

Referring now to FIGS. 4A-4C, it can be seen that working portion 25 is movable between a (first) insertion configuration (FIG. 4A) and a (second) deployed configuration (FIG. 4B). In the insertion configuration of FIG. 4A, each tissue-compression member 30 and 32 has laterally-extending elements in a (first) repose position. In the deployed configuration of FIG. 4B, the tissue-compression members 30 and 32 have laterally-extending elements in a (second) articulated position. For example, member 30 has three laterally-extending elements or arm portions 45a-45c that flex outwardly away from axis 15 of working portion 25. Each arm is shown with living-type hinges wherein the entire member 30 is of a resilient plastic. In general, proximal sliding movement of inner sleeve 20 within bore 18 of outer sleeve 10 by means of moving handle portion 26 in the proximal direction relative to handle 16 (FIGS. 1-2) causes proximal end 40a and distal end 40b of member 30 to be compressed axially toward one another resulting in arms 45a-45c flexing at living hinge points 46, 47 and 48 (collectively). Tissue-compression member 32 has three cooperating arm portions 47a-47c that flex outwardly (similar to counterpart member 30) at equivalent hinge points (not numbered). It should be appreciated that the number of arms 45a-45c and 47a-47c may be from one to four or more and for convenience are shown as numbering three. FIGS. 3 and 4B show that distal end 22 of inner sleeve 20 is coupled to shaft portion 50 and shaft 50 is fixed to distal end 42b of member 32 thus allowing proximal end 42a (and bore portion 52 therein) of member 32 to slide over shaft 50.

FIG. 4B. shows that each laterally-extending elements or arms 45a-45c of member 30 have radiused working faces 55 (collectively) that are somewhat rounded for engaging tissue such that the tissue will not be penetrated. Similarly, arms 47a-47c of member 32 have radiused working faces 56 (collectively).

Means are thus provided for altering the extracellular fluid (ECF) content of tissue engaged by the laterally-extending elements of working end 25 by tissue compression. As can be seen in FIGS. 4A-4B, arms 45a-45c and 47a-47c define gap 58 therebetween for engaging target tissue and thereafter compressing the targeted tissue sites. Additional axial reciprocating means are provided for reducing the axial dimension of gap 58 after the arms are deployed as shown in FIG. 4B. By comparing FIGS. 4B and 4C, it can be seen that gap 58 is capable of moving from initial dimension A to reduced dimension A' when inner sleeve 20 is moved axially relative to outer sleeve 10 and overcomes the spring constant of helically wound extension spring 59 that is disposed between opposing annular faces (60a and 60b) of members 30 and 32, respectively (see FIG. 3). The spring constant of spring 59 is stronger than the collective spring constants of the living hinges (e.g., 47-49) of the arm elements described above. Thus, initial proximal axial movement of inner sleeve 20 relative to outer sleeve 10 causes arms 45a-45c and 47a-47 to deploy (FIG. 4B). Additional proximal axial movement of inner sleeve 20 relative to outer sleeve 10 causes working faces 55 and 56 of the arms to move closer axially (FIG. 4C).

It should be appreciated that a variety of spring loading mechanisms may be used to actuate the arm elements in a particular sequence. Preferably, the first proximal axial movement of inner sleeve 20 relative to outer sleeve 10 will causes arms 47a-47c of member 32 to deploy. The second or next proximal axial movement of inner sleeve 20 relative to outer sleeve 10 will cause arms 45a-45c of member 30 to deploy. In other words, two steps may be required to move working end 25 to the configuration of FIG. 4B from the configuration of FIG. 4A. Finally, the next or third proximal axial movement of inner sleeve 20 relative to outer sleeve 10 will cause gap 58 to be reduced from A to A' (see FIG. 4C). The control end (handles 16 and 26) of the device preferably may be locked (not shown) by any suitable means to maintain members 30 and 32 in the articulated position. Further, the control end may comprise any suitable mechanism for actuating the working end, e.g., a lever arm, trigger, etc., and is shown as cooperating slidable handles 16 and 26 for convenience only.

Figure 5:
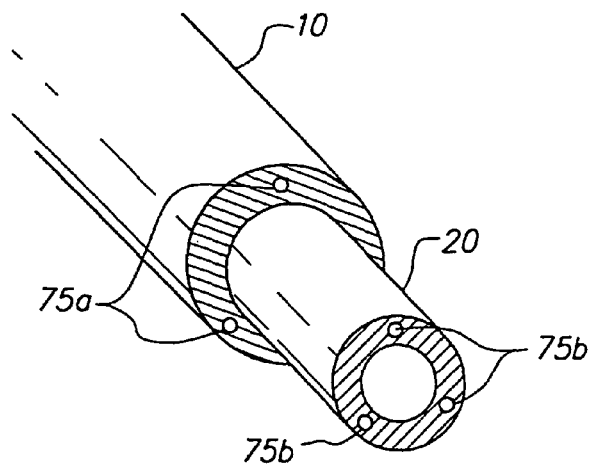
FIG. 5 is a transverse sectional view of the device of FIG. 1 taken along line 5-5 of FIG. 4A.

Thermal energy delivery means are provided for thermally treating target tissue engaged or compressed between working faces 55 and 56. Conductive electrodes or electrode arrays 70 and 72 (collectively) for delivering RF energy are shown carried in respective working faces 55 and 56. Each electrode preferably is individually controlled as described further below. FIG. 5 shows that the walls of outer sleeve 10 and inner sleeve 20 have embedded therein individual current-carrying wires 75a and 75b that supply RF energy to each conductive electrode. Both groups of the electrodes 70 and 72 are shown in FIGS. 4A-4C as being bipolar but the electrodes may be operated in a mono-polar fashion with a groundplate (not shown). Electrode material may include gold, nickel titanium, platinum, stainless steel, aluminum and copper. Referring to FIGS. 1-2, electrical cables 77 (collectively) are connected to an RF energy source through a controller described below which is adapted to deliver energy to electrodes 70 and 72.

Referring back to FIGS. 3 and 4A-4C, it can be seen that a sensor array of individual sensors 80 (collectively) is provided in a spaced relationship around working end 25 and arms 45a-45c and 47a-47c. The sensor array typically will include temperature sensors, thermisters (temperature sensors that have resistances that vary with the temperature level) and/or impedance sensing elements that measure tissue impedance in various conventional manners, although impedance measurement may obtained through electrodes 70 and 72 without resort to dedicated electrodes and circuits for impedance measuring purposes.

Figure 6:
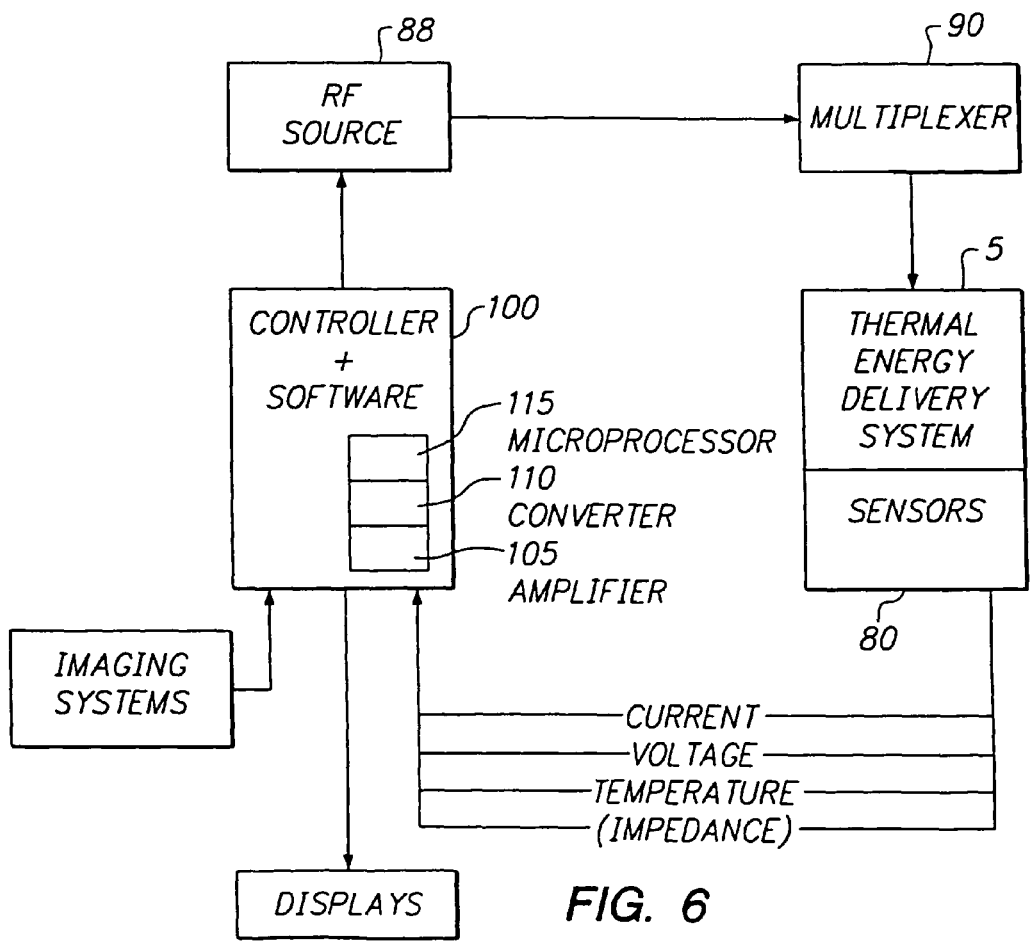
FIG. 6 is a block diagram of a control portion of the invention that includes a computer controller and energy source.

The electromagnetic energy delivery source 88, for example, may be assumed to be an RF generator delivering energy to electrode 70 and 72. A multiplexer 90 is depicted in FIG. 6 which is operatively connected to each electrode for measuring current, voltage and temperature at thermal sensors 80 (collectively) spaced around working end 25 or individually associated with each electrode.

Multiplexer 90 is driven by a controller 100 which typically is a digital computer with appropriate software. The controller typically would include a CPU coupled to the multiplexer through a bus. On the controller system, there may be a keyboard, disk drive or other non-volatile memory system, displays as are well known in the art for operating the system. Such an operator interface may include various types of imaging systems for observing the treatment such as thermal or infrared sensed displays, ultrasonic imaging displays or impedance monitoring displays.

For such an operator interface, current supplied to individual electrodes along with voltage may be used to calculate impedance. Thermal sensors 80 carried in a position proximate to electrodes 70 and 72 together with thermal sensors 102 positioned within RF generator are adapted to measure energy delivery (current and voltage) to each electrode at a treatment site during a treatment cycle. The output measured by thermal sensors 80 and 102 are fed to controller 100 to control the delivery of power to each electrode site. The controller 100 thus can be programmed to control temperature and power such that a certain particular temperature is never exceeded at the treatment site. The operator further can set the desired temperature which can be maintained. The controller has a timing feature further providing the operator with the capability of maintaining a particular temperature at an electrode site for a particular length of time. A power delivery profile may be incorporated into controller 100 as well as a pre-set for delivering a particular amount of energy. A feedback system or feedback circuitry can be operatively connected to impedance measuring system, the temperature sensors and other indicators at the controller 100 or within the power source 88.

The controller software and circuitry, together with the feedback circuitry, thus is capable of full process monitoring and control of following process variables: (i) power delivery; (ii) parameters of selected particular treatment cycle, (iii) mono-polar or bi-polar energy delivery; and (iv) flow rate of coolant to insulator wall portion of the introducer sheath if cooling is provided. Further, the controller can determine when the treatment is completed based on time, temperature or impedance or any combination thereof. The above-listed process variables can be controlled and varied in response to tissue temperatures measured at multiple sites on tissue surfaces in contact with the device as well as by impedance to current flow at measured at each electrode which indicates the current carrying capability of the tissue during the treatment process. Additionally, controller 100 can provide multiplexing, can monitor circuit continuity for each electrode and determine which electrode is delivering energy.

FIG. 6 shows a block diagram of a particular embodiment of control circuitry. Note that thermal sensors can be thermisters which provide differing resistance levels depending on temperature. Amplifier 105 can be a conventional analog differential amplifier for use with thermisters and transducers. The output of amplifier 105 is sequentially connected by analog multiplexer 90 to the input of analog digital converter 110. The output of amplifier 105 is a particular voltage that represents the respective sensed temperatures. The digitized amplifier output voltages are supplied to microprocessor 115. Microprocessor 115 thereafter calculates the temperature and/or impedance of the tissue site in question. Microprocessor 115 sequentially receives and stores digital data representing impedance and temperature values. Each digital value received by microprocessor corresponds to a different temperature or impedance at a particular site.

The temperature and impedance values may be displayed on operator interface as numerical values. The temperature and impedance values also are compared by microprocessor 115 with pre-programmed temperature, and impedance limits. When the measured temperature value or impedance value at a particular site exceeds a pre-determined limit, a warning or other indication is given on operator interface and delivery of electromagnetic to a particular electrode site or area can be decreased or multiplexed to another electrode. A control signal from the microprocessor may reduce the power level at the generator or power source, or de-energize the power delivery to any particular electrode site. Controller receives and stores digital values which represent temperatures and impedance sent from the electrode and sensor sites. Calculated wall surface temperatures within the urethra and the bladder may be forwarded by controller 100 to the display and compared to a predetermined limit to activate a warning indicator on the display.

II. Method of Use of Type "A" Embodiment

Operation and use of the catheter shown in FIG. 1 in performing a method of the present invention can be described briefly as follows. Assume that the physician wishes to (i) initially thermally treat target tissues around the patient's bladder sphincter to alter the cellular architecture therein; and optionally (ii) to subsequently thermally treat the target tissues to contract the extracellular collagen matrix induced therein by the initial thermal treatment.

Figure 7A:
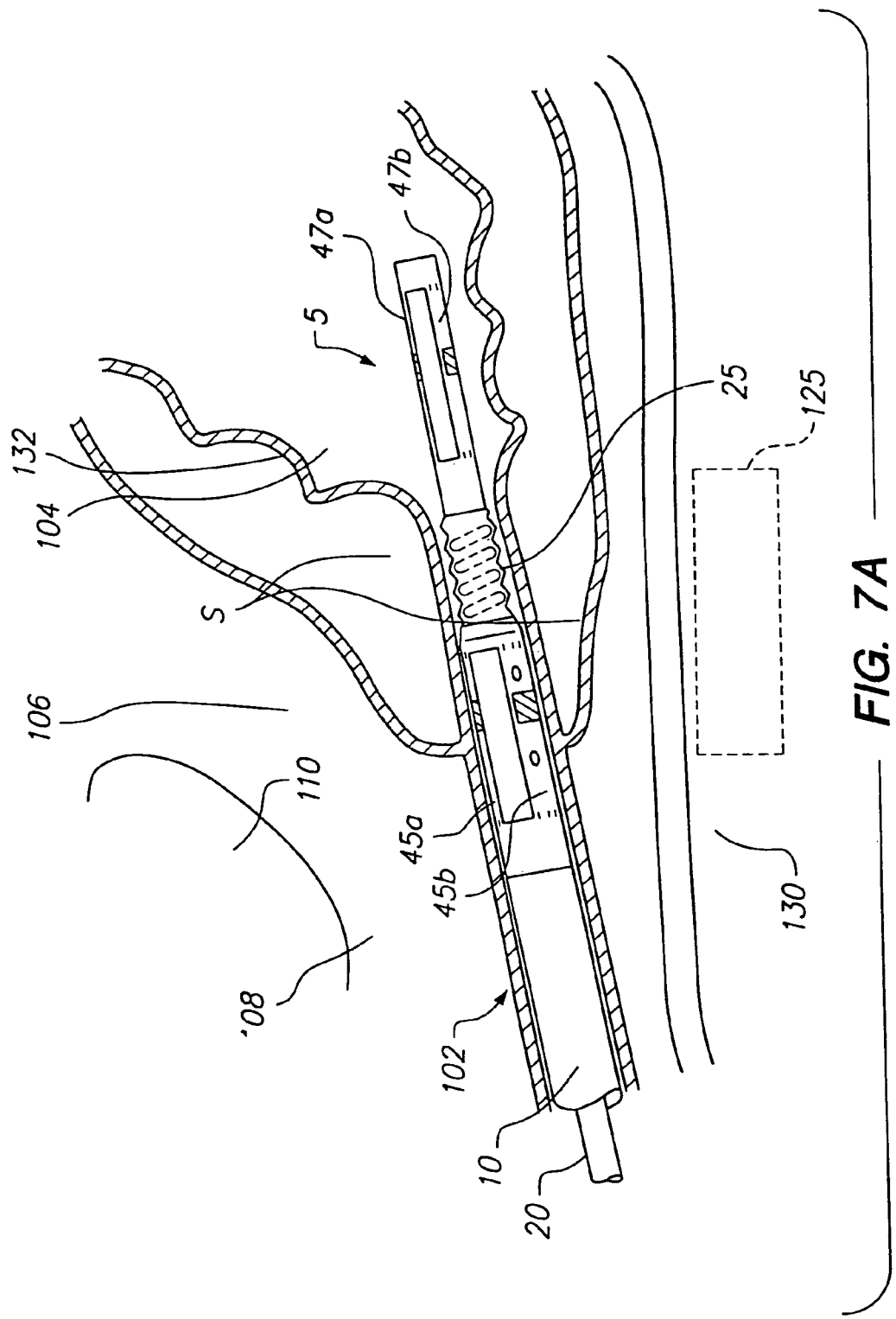
FIGS. 7A-7D are a sequence of sectional views of a patient's bladder and urethra showing the manner in which the instrument of FIG. 1 is illustratively utilized to perform a method of the invention in thermally treating tissue around the patient's sphincter.

FIG. 7A is a schematic cross-sectional drawing of the lower female anatomy during use of the instrument and method of the invention. The urethra 102 extends from the bladder 104 within fat pad 106. Urinary incontinence is a condition characterized by a malfunctioning sphincter 108 often caused by movement or slippage of the bladder relative to pubic bone 110 within pad 106 and other regional anatomic structures. As shown in FIG. 7A, in the method of this invention, the catheter system 5 is passed upwardly through the urethra 102 into the bladder 104 in the insertion configuration (see FIG. 1). The position of working portion 25 is precisely controlled using an ultrasound image, for example, obtained from signals received from the conventional ultrasound transducer 125 inserted into vagina 130 adjacent to the bladder or with an ultrasound transducer positioned outside the body (not shown). The catheter system alternatively may be introduced over a fiberscope previously inserted into the patient's urethra (not shown).

Figure 7B:
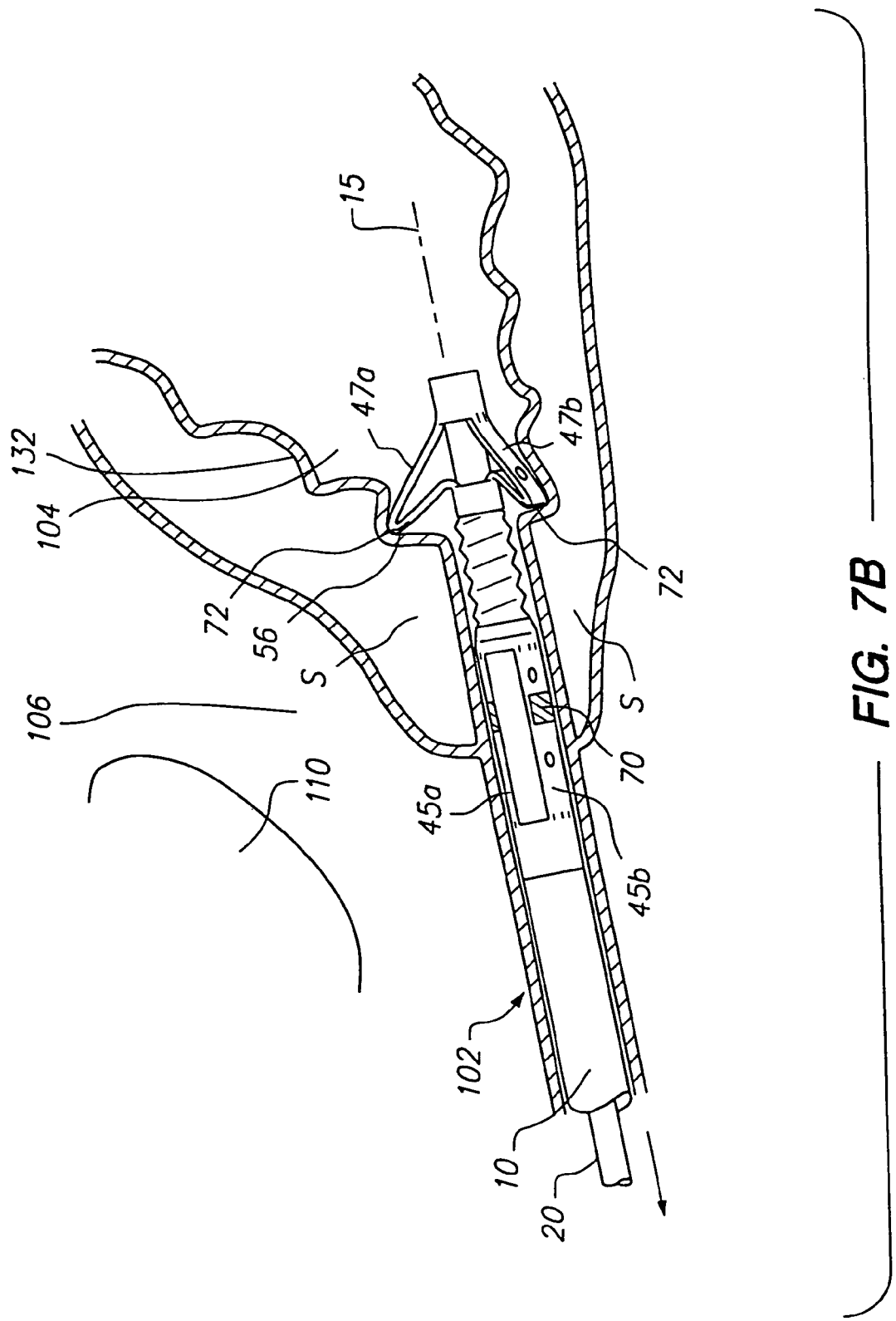

With the distal or terminal portion of working end 25 in the bladder, the surgeon then moves handle portion 26 (FIG. 1) and inner sleeve 20 proximally a first distance relative to outer sleeve 10 and handle 16. As can be seen in FIG. 7B, such actuation moves arm elements 47a-47c laterally away from or outward relative to axis 15 to a first deployed position of working portion 25 thus pressing working faces 56 (and electrodes 72) of the arms against walls 132 of bladder 104.

Figure 7C:
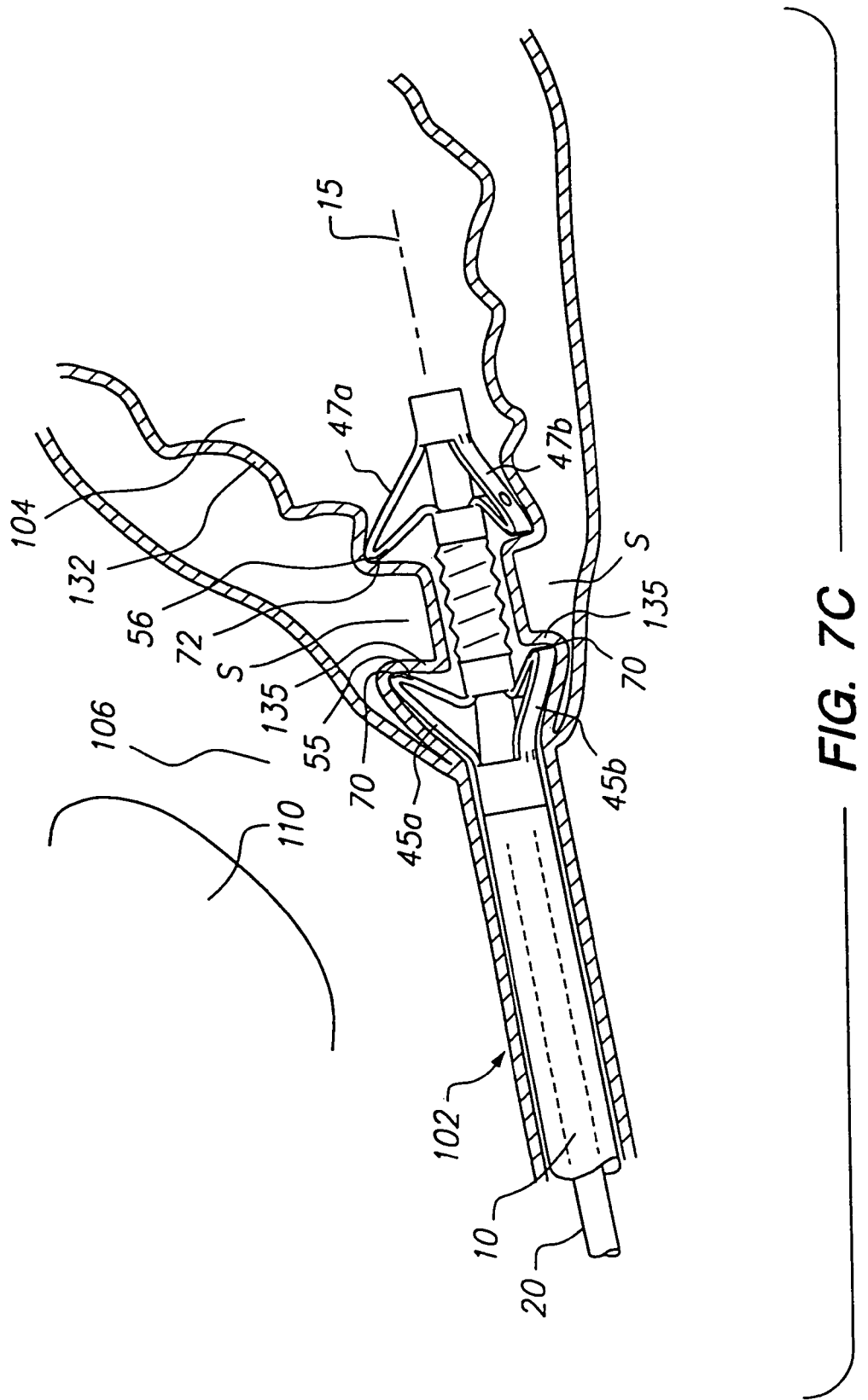
Figure 7D:
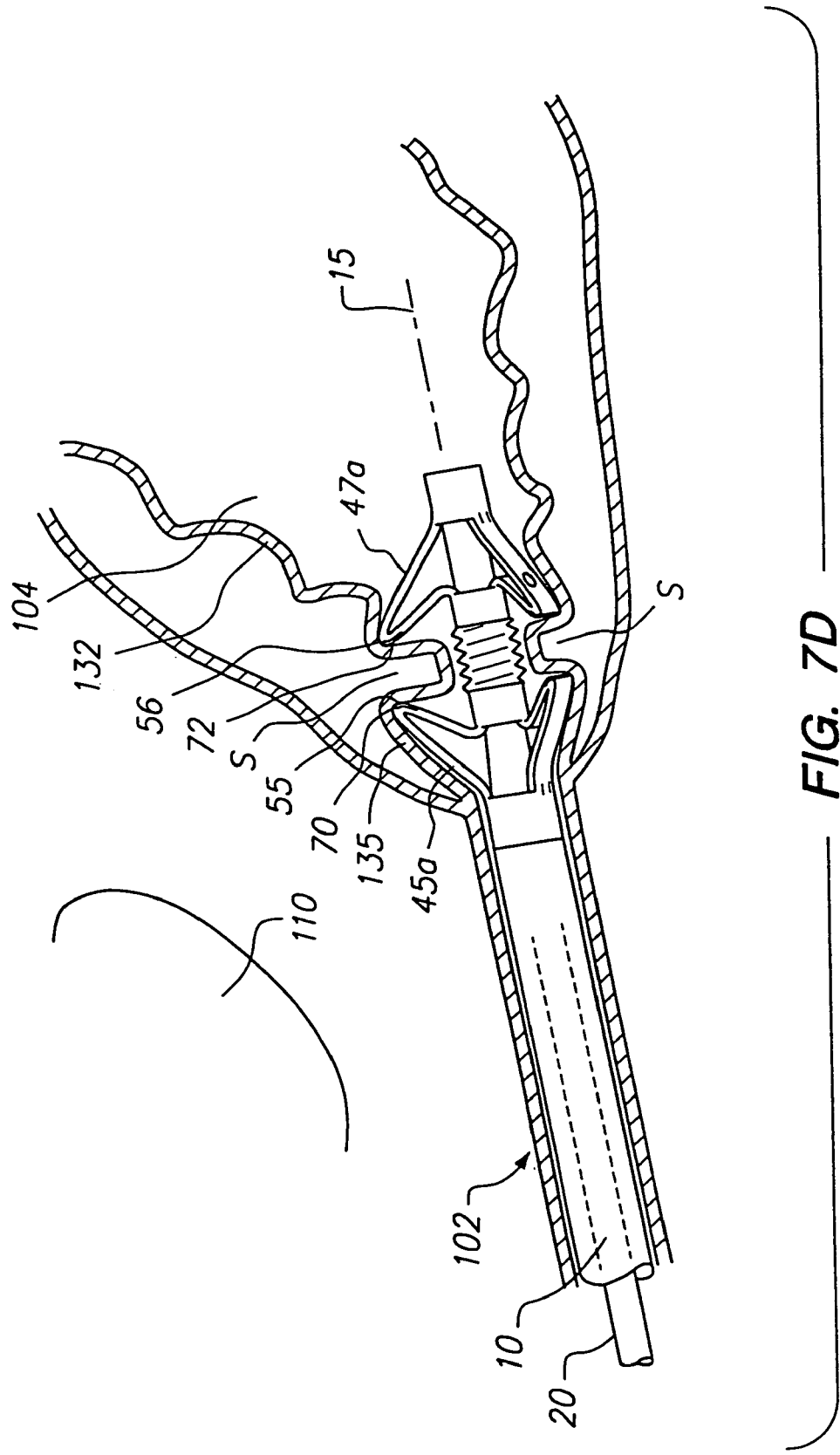

Thereafter, the physician may angularly rotate the entire catheter about its axis td orient one or more of the arm elements toward tissues to be treated. The physician then moves handle portion 26 (FIG. 1) and inner sleeve 20 proximally a second distance relative to outer sleeve 10. As can be seen in FIG. 7C, such further actuation moves arm elements 45a-45c to a second deployed position being within the urethra 102 such that working faces 55 of the these arms along with electrodes 70 are laterally extended somewhat deep into the target tissues indicated at S. The curvature and radiusing of working faces 50 insure that the arms do not penetrate the walls 135 of the urethra. Finally, as shown in FIG. 7D, the physician moves handle portion 26 and inner sleeve 20 proximally a third distance relative to outer sleeve 10 thereby moving arm elements 45a-45c and 47a-47c (a third deployed position) closer together to compress target tissue S therebetween (see FIG. 4C).

Figure 8:
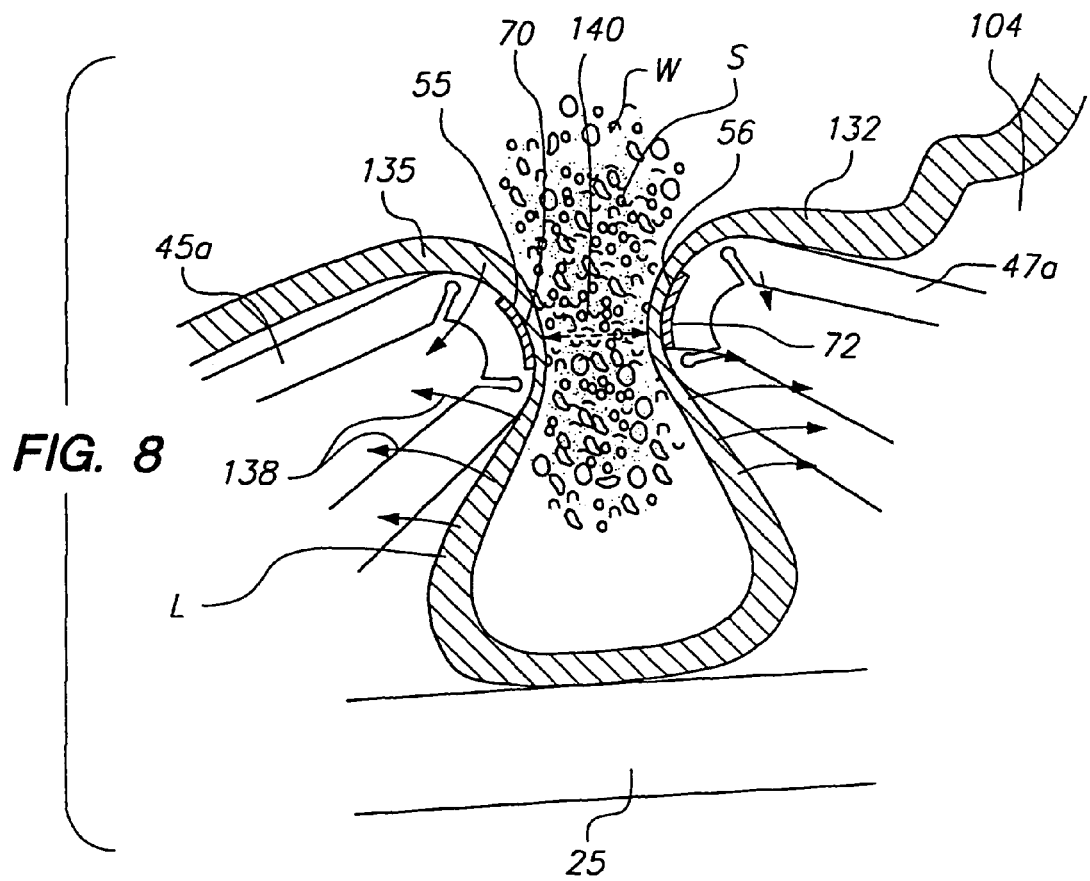
FIG. 8 is an enlarged sectional view of the compression of target tissue and the delivery thermal energy taken along line 8-8 of FIG. 7D.

Referring to FIG. 8, the compression of target tissue S between working faces 55 and 56 reduces the extracellular fluid (ECF) content in tissue S thus increasing tissue S's resistance to RF current. Thus, delivery of RF current through either electrodes 70 or 72 will allow tissue S to be elevated to $T_{cd}$ (temperature or cell damage) to induce the injury healing response while surface layer L remains at a lower temperature such that the surface layers will not be ablated, principally due to the fact that surface layer L has a lower resistance (R) due to its higher ECF level as well as the fact that evaporative and convective forces further reduce the temperature of surface layer L indicated by arrows 138.

Still referring to FIG. 8, it further should be appreciated that reduction of ECF level in target tissue S tends to increase the ECF level in tissues W just outward or away from the most compressed target tissue S. The non-compressed tissue W thus will have a lesser resistance to RF current (due to increased ECF content) and readily conducts the RF energy to target tissue S. Thus, a temperature gradient will exist where the center of the region of target tissue S will be elevated to the highest temperature (a higher current density) than region W. Surface layer L will have the lowest temperature due to increased ECF levels as was tissue W as well as the evaporative/convective effects affecting layer L mentioned above. In other words, the compression of target tissue caused it to act as a "fuse" or "fuse point" surrounded by more conductive tissue volumes or layers. The center point 140 of target tissue S is thus a focus of the heating which is similar to a fuse.

Electrodes 70 and 72 on the arm elements are energized from RF energy source 88 by actuation of a switch in the control end (handle 16 or 26) of the catheter system 5 or from a foot pedal or other suitable means. Preferably, the time and/or power levels are preset by the controller 100. The RF energy from energy source 88 is delivered to the target tissue S for a pre-selected time. Impedance also is monitored, and when or if it exceeds a preset value, the energy source can be reduced or terminated automatically by controller 100. The temperature of surfaces of working portion 25 adjacent the urethral wall 135 and adjacent to the bladder wall 122 are also monitored using temperature sensors attached to these components to precisely control the treatment parameters and prevent excessive heating of surface tissue layers L.

After target tissue S has sustained cell damage at the desired level, the physician may collapse the arms 45a-45c and 47a-47c back onto working portion and either rotate the catheter slightly and repeat the treatment or remove the device from the patient's body.

It should be appreciated that arm elements, although shown as angularly symmetric, may be asymmetric thus delivering energy to a target sites in a pre-determined asymmetric pattern.

One or more temperature sensors 80, which can be conventional thermistors, thermocouples or even optical fibers communicating with external sensors, are positioned along the catheter or arm elements to provide a temperature profile of the urethra adjacent to and preferably on both sides the electrodes 70 and 72. This temperature profile can be used by the operator to prevent the temperature of the urethral wall or bladder wall from reaching level which would cause surface ablation. The RF energy thus exposes the target tissue S to controlled heating to $T_{cd}$ (temperature of cell damage) of approximately 45° C. to 65° C. Preferably, the temperature range is from 45° C. to 55° C. Still more preferably, the temperature range is from 45° C. to 50° C.

Figure 9:
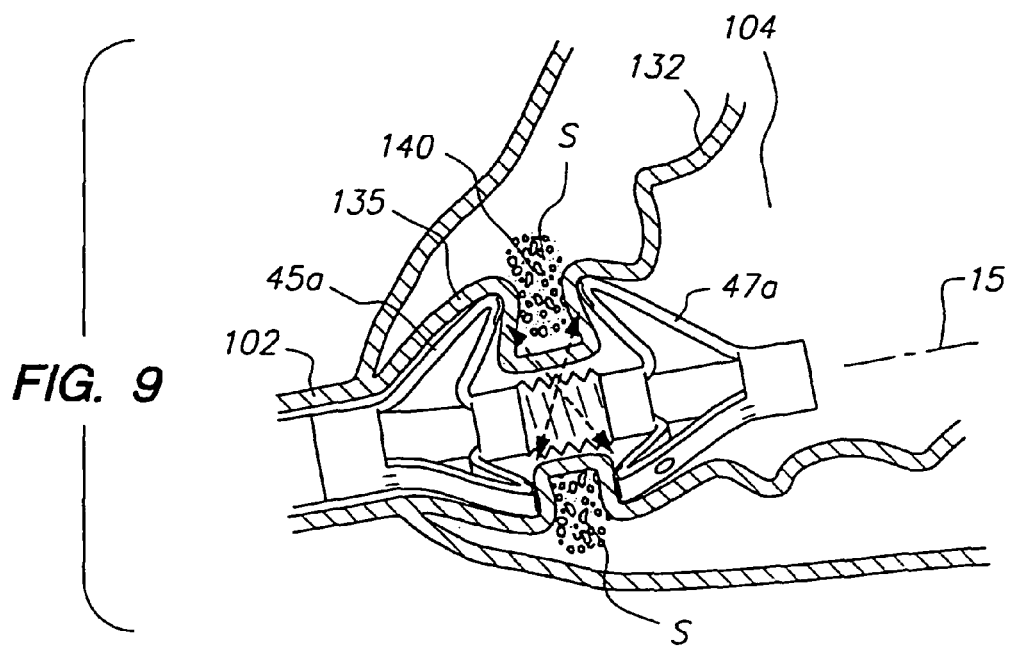
FIG. 9 is another enlarged sectional view of the compression of target tissues similar to FIGS. 7D and 9 showing optional current vectors.

The RF current typically is delivered between opposing electrodes 70 and 72 in a bi-polar manner as shown by broken arrows in FIG. 8. In certain selected instances, more directed cell damage can be obtained by alternating the bi-polar flow of current in various vectors indicated by broken arrows in FIG. 9. In other instances, one or more of the electrodes may act as a mono-polar electrode and a delivery energy to a grounding plate (not shown). The RF treatment is continued until the cells in the target tissue S have been damaged as indicated by dotted lines in FIGS. 8 and 9. The cell damage induces the body's injury healing response which thereafter populates the extracellular compartment with a collagen fiber matrix having the effect of bulking tissue and reducing the flexibility of tissues as described above. Such tissue bulking or tissue stiffening causes extraluminal pressures around the sphincter and helps restore the sphincter's ability to pinch off urine flow. A similar procedure may be performed to enhance extraluminal pressures around the sphincter of the esophagus.

This procedure is unique in that it is the first transluminal procedure which selectively provides the ability to limit the treatment to the extraluminal target tissues and spares the normal tissue of the organ wall from excessive temperatures. This procedure also minimizes the trauma sustained by tissues surrounding urethra 102, especially when compared to previously known procedures. The procedure may be carried out under local anesthesia only, depending upon the rate of energy delivery and degree of pain sensation experienced by the patient. When local anesthetic is adequate, the procedure can be performed in the physician's office. Such a procedure still could be provided on an outpatient basis and would require a short term (1-3 hour) observation. If the procedure and patient require greater pain control, then spinal anesthesia or a general anesthesia may be used which would mandate the procedure be carried out in the operating room.

Following a therapeutic cycle, the patient may return to normal activities with careful monitoring of the sphincter function. Thereafter, perhaps on a bi-weekly or monthly basis, the identical treatment cycle may be repeated in a one or more subsequent cycles until the desired reduction in tissue flexibility and pressure on the sphincter is achieved. It is believed that such periodic treatments (e.g., from 1 to 3 treatments over a period of a few weeks) may be best suited to stiffen target tissue S and to correct sphincter function.

In the subsequent treatment cycles, the temperature profile may be programmed to attain the slightly higher level Tsc necessary to shrink collagen fibers in the extracellular collagen matrix induced by the original treatment. The controller 100 and preprogrammed therapy cycle still will allow the temperature of the organ wall to be low enough so as to prevent surface ablation by making the energy delivery intermittent. The RF energy thus exposes the target tissue S to controlled heating to Tsc (temperature necessary to shrink collagen) of approximately 50° C. to 80° C. More preferably, the RF energy exposes tissue S to controlled heating of approximately 60° C. to 70° C. Still more preferably, the RF energy exposes tissue S to controlled heating of approximately 65° C. to 70° C.

III. Type "B" Embodiment of Thermal Energy Deliver, (TED) Device

Figure 10A:
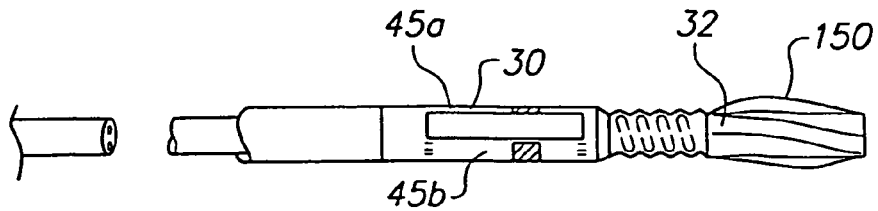
FIGS. 10A-10C are plan views of a working portion of a Type "B" embodiment of thermal energy delivery device.
Figure 10B:
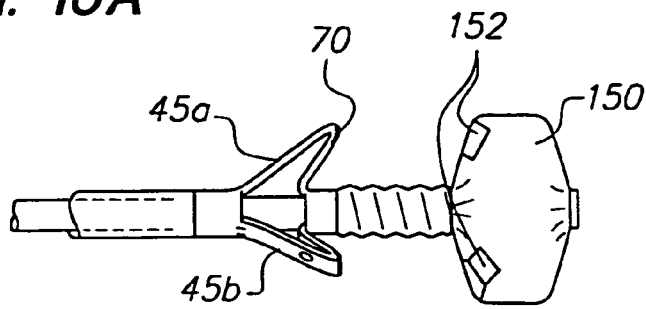
Figure 10C:
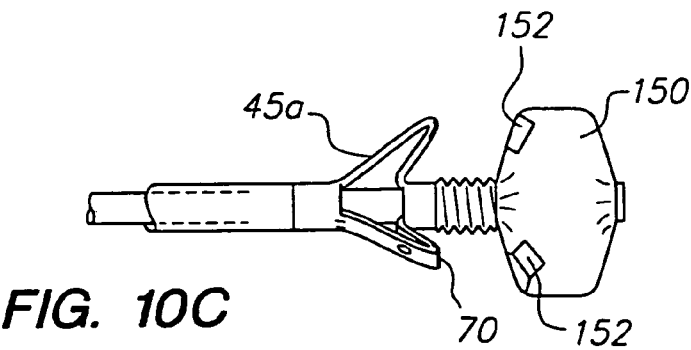

Referring to FIGS. 10A-10C, a Type "B" embodiment of the present invention is shown that is adapted for transluminal introduction and is similar in most respects to the first-described embodiment. Like reference numerals refer to like components of the Type "A" and Type "B" devices.

The Type "B" device differs principally in that the distal tissue compression member 32 that is coupled to the distal end 22 of inner sleeve 20 carries an inflatable structure 150 rather than laterally extendable elements. The inflatable structure 150 communicates with any conventional pressure source (e.g., a syringe) through lumen 25 in the wall of inner sleeve 20 (FIG. 10). Preferably, inflatable structure 150 is of a non-compliant material such as PET but also may be an elastomer such as latex or silicone.

Figure 11A:
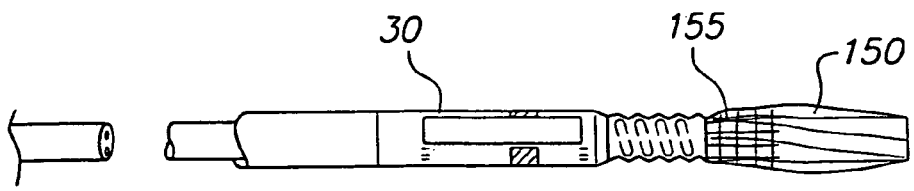
FIGS. 11A-11B are plan views of an alternative embodiment of the working portion of the Type "B" embodiment of FIG. 10A.
Figure 11B:
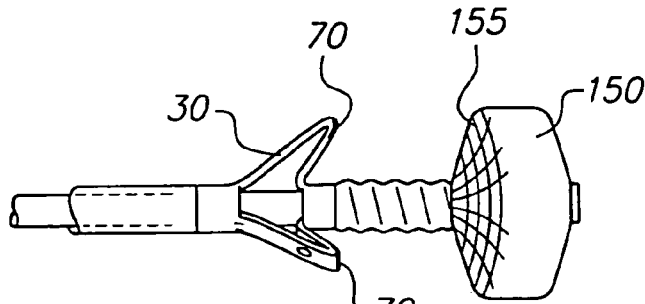

In use, the Type "B" embodiment is used in a fashion similar to that described above. First, the catheter is introduced into the organ and then inflatable structure 150 is expanded. Thereafter, the proximal arms 45a-45c are extended laterally to compress tissue between the arms 45a-45c and inflatable structure 150. RF energy may be delivered in a monopolar fashion. Alternatively, the surface of the inflatable structure 150 may have a plurality of opposing electrodes 152 and the RF energy may be delivered in a bi-polar fashion as described previously. Another alternative embodiment of inflatable structure 150 could include a metallic mesh 155 as a return electrode covering a substantial portion of the surface of the inflatable structure facing electrodes 60 (see FIGS. 11A-11B).

IV. Type "C" Embodiment of Thermal Energy Delivery (TED) Device

Figures 12A, 12B:
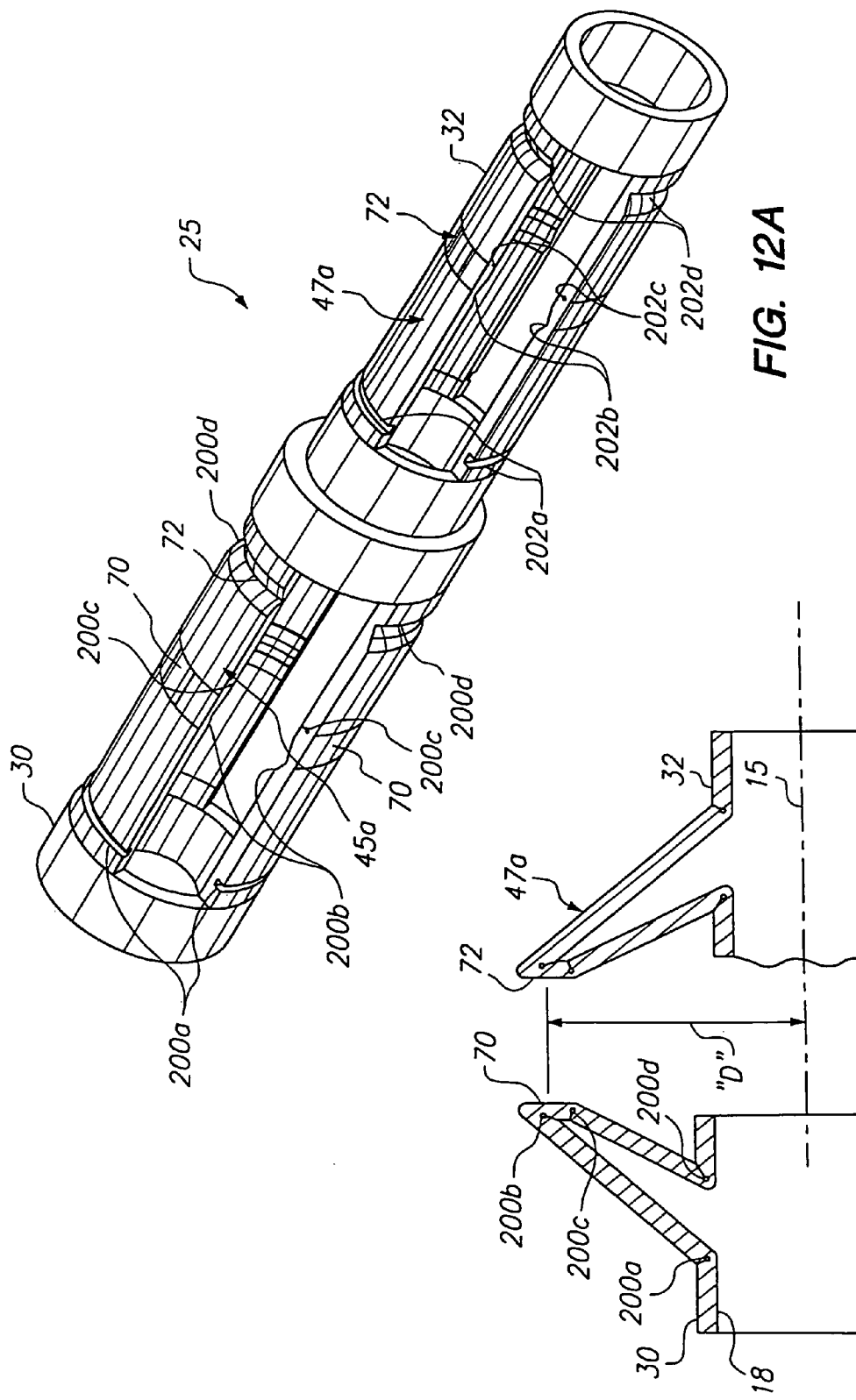
FIGS. 12A-12B are perspective and sectional views of a working portion of a Type "C" embodiment of thermal energy delivery device.

Referring to FIGS. 12A-12B, a Type "C" embodiment of the present invention is shown that is very similar to the first-described Type "A" embodiment. Like reference numerals refer to like at components of the Type "A" device. This Type "C" working end 25 has the spring mechanism for sequencing the articulation of laterally extending elements 45a-45c and 47a-47c eliminated from the working end. The spring mechanism may be moved to the handle end or control end of the instrument (not shown).

FIGS. 12A and 12B show more in particular how each laterally-extending element may be configured with four living hinges points 200a, 200b, 200c and 200d to allow electrodes 70 to assume a face angle at about 900 to axis 15. Each living hinge point comprises a reduced sectional dimension of the resilient plastic of the member. Similarly, four living hinges points 202a, 202b, 202c, and 202d allow electrodes 72 to assume a face angle at about 90° relative to axis 15. FIG. 12B shows that by varying the lengths of the certain segments of the laterally extending elements 45a and 47a, electrodes 70 and 72 may be aligned and opposed at a similar distance D from axis 15. In use, the Type "C" embodiment is used in a fashion similar as described above.

This disclosure is illustrative and not limiting. Although specific features of the invention are shown in some drawings and not in others, this is for convenience only and any feature may be combined with another in accordance, with the invention and are intended to fall within the scope of the appended claims. Other aspects of the invention are apparent from the drawings and accompanying descriptions of the instrument and techniques of this invention which will be readily apparent to a person skilled in the art that this procedure can be used in many areas of the body in percutaneous approaches as well as approaches through body orifices to thermally treat tissues around an anatomic duct.

What is claimed is:

1. An apparatus to treat a target tissue volume at or near a sphincter comprising
   a radiofrequency energy delivery device having an elongated axis adapted to extend through an esophagus to a targeted tissue site at or near a sphincter, the radiofrequency energy delivery device including a working end sized and configured for transluminal introduction into a patient, the delivery device further including a tissue compression member deployable to provide compression of target tissue at or near a sphincter, said tissue compression member comprising at least two radially extending elements movable toward each other along the axis to capture a volume of tissue therebetween, and
   a radiofrequency energy source coupleable to the delivery device to deliver radiofrequency energy to the target tissue to reduce laxity in the target tissue.

* * * * *